(12) United States Patent
Mijolovic et al.

(10) Patent No.: US 8,519,084 B2
(45) Date of Patent: Aug. 27, 2013

(54) USE OF A C11 DIOL OR C11 DIOL MIXTURE FOR PRODUCING POLYMERS

(75) Inventors: Darijo Mijolovic, Mannheim (DE); Sebastien Garnier, Weinheim (DE); Qiang Miao, Mannheim (DE); Maria Guixa Guardia, Mannheim (DE); Gerd-Dieter Tebben, Mannheim (DE); Dag Wiebelhaus, Neustadt (DE)

(73) Assignee: BASF SE, Ludwigshafen (DE)

( * ) Notice: Subject to any disclaimer, the term of this patent is extended or adjusted under 35 U.S.C. 154(b) by 329 days.

(21) Appl. No.: 12/997,805

(22) PCT Filed: Jun. 10, 2009

(86) PCT No.: PCT/EP2009/057133
§ 371 (c)(1),
(2), (4) Date: Dec. 13, 2010

(87) PCT Pub. No.: WO2009/153193
PCT Pub. Date: Dec. 23, 2009

(65) Prior Publication Data
US 2011/0130514 A1 Jun. 2, 2011

(30) Foreign Application Priority Data
Jun. 16, 2008 (EP) ..................................... 08158308

(51) Int. Cl.
*C08G 63/02* (2006.01)

(52) U.S. Cl.
USPC ........ 528/272; 528/425; 528/302; 528/308.7; 528/323; 528/354; 528/85; 528/370; 568/853; 524/605; 428/334; 428/141; 428/215; 428/214; 428/323; 428/337; 428/40.1; 428/423.7; 428/480

(58) Field of Classification Search
USPC ............. 528/425, 302, 308.7, 323, 354, 370, 528/85, 272; 428/334, 141, 214, 215, 323, 428/337, 40.1, 423.7, 480; 524/605; 568/853
See application file for complete search history.

(56) References Cited

U.S. PATENT DOCUMENTS

| | | | |
|---|---|---|---|
| 2002/0098344 A1* | 7/2002 | Mizuno et al. | 428/334 |
| 2003/0092832 A1* | 5/2003 | Tanaka et al. | 524/589 |
| 2008/0118855 A1 | 5/2008 | Nakayama et al. | |

FOREIGN PATENT DOCUMENTS

| | | |
|---|---|---|
| DE | 195 24 971 | 1/1997 |
| EP | 0 562 578 | 9/1993 |
| EP | 1 131 372 | 9/2001 |
| JP | 03 161452 | 7/1991 |
| WO | 00 23495 | 4/2000 |
| WO | 03 018192 | 3/2003 |
| WO | 2004 092097 | 10/2004 |

OTHER PUBLICATIONS

International Search Report issued Aug. 10, 2009 in PCT/EP09/057133 filed Jun. 10, 2009.
U.S. Appl. No. 13/003,911, filed Jan. 13, 2011, Mijolovic, et al.
U.S. Appl. No. 13/061,743, filed Mar. 2, 2011, Mijolovic, et al.
U.S. Appl. No. 13/159,761, filed Jun. 14, 2011, Rohde, et al.

* cited by examiner

*Primary Examiner* — Shane Fang
(74) *Attorney, Agent, or Firm* — Oblon, Spivak, McClelland, Maier & Neustadt, L.L.P.

(57) ABSTRACT

A polymer obtainable by polycondensation or polyaddition of monomeric compounds, wherefor accompanying use is made as monomeric compound of 2-(2-methylbutyl)-2-propyl-1,3-propanediol of the formula I or its alkoxylated derivatives (also referred to collectively below as C11 diol).

15 Claims, No Drawings

USE OF A C11 DIOL OR C11 DIOL MIXTURE FOR PRODUCING POLYMERS

The invention relates to a polymer which is obtainable by polycondensation or polyaddition of monomeric compounds, wherefor accompanying use is made as monomeric compound of
2-(2-methylbutyl)-2-propyl-1,3-propanediol of the formula I

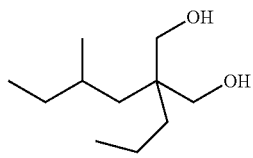

or its alkoxylated derivatives (also referred to collectively below as C11 diol).

Diols are needed for the preparation of polymers, e.g., polyesters or polyurethanes. EP-A 562 578 describes, for example, the use of different cyclohexanediols such as 1,4-cyclohexanedimethanol or 1,4-cyclohexanediethanol to prepare polyesters.

The use of 2-pentyl-2-propyl-1,3-propanediol of the formula II for preparing polyesters is known from JP HEI 03-161452.

In principle there is a desire to improve the performance properties of polymers in their various uses.

Where the polymers are used as binders in coating compositions, adhesives or sealants, the viscosity is particularly important, whether it be the melt viscosity (100% systems) or the solution viscosity (polymer solutions). For film-forming applications, the coatings produced ought to have good mechanical properties, such as impact toughness and elasticity, high scratch resistance and impact strength, high resistance to water, solvents, grease, chemicals, and environmental effects, and also a high gloss.

It was an object of the present invention to provide such polymers.

Found accordingly have been the polymers defined at the outset and also their use as binders in coating compositions, sealants or adhesives.

The C11 Diol or C11 Diol Mixture

The polymer of the invention is prepared using, in accompaniment to other monomeric compounds, 2-(2-methylbutyl)-2-propyl-1,3-propanediol of the formula I

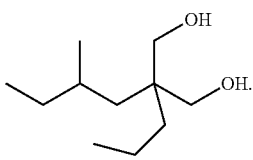

In the text below, the intention when referring to 2-(2-methylbutyl)-2-propyl-1,3-propanediol of the formula I and also when referring to the 2-pentyl-2-propyl-1,3-propanediol below, of the formula II, is always that the alkoxylated derivatives should be included as well. The diols may more particularly be alkoxylated with ethylene oxide or propylene oxide or else mixtures thereof the alcohol groups may be alkoxylated, for example, with 1 to 20, more particularly 1 to 10, alkoxy groups.

In one preferred embodiment the two diols are not alkoxylated.

Preferably, in addition to 2-(2-methylbutyl)-2-propyl-1,3-propanediol of the formula I, it is used in a mixture with 2-pentyl-2-propyl-1,3-propanediol of the formula II

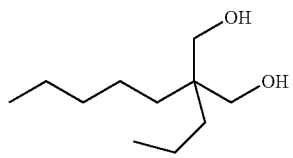

as a monomeric compound to prepare the polymers of the invention.

2-(2-Methylbutyl)-2-propyl-1,3-propanediol of the formula I is also referred to below as C11 diol; 2-(2-methylbutyl)-2-propyl-1,3-propanediol and 2-pentyl-2-propyl-1,3-propanediol are also referred to below as C11 diol mixture.

The C11 diol mixture may comprise, for example,

1% to 99% by weight, more particularly 5% to 95% by weight, of 2-(2-methylbutyl)-2-propyl-1,3-propanediol and 1% to 99% by weight, more particularly 5% to 95% by weight, of 2-pentyl-2-propyl-1,3-propanediol, the percentages by weight being based on the sum by weight of the stated diols.

The C11 diol mixture comprises preferably

1% to 50%, more particularly 2% to 30%, more preferably 5% to 20%, and very preferably 7% to 15% by weight of 2-(2-methylbutyl)-2-propyl-1,3-propanediol and correspondingly 50% to 99%, more particularly 70% to 98%, more preferably 80% to 95%, and very preferably 85% to 93% by weight of 2-pentyl-2-propyl-1,3-propanediol, the weight percentages being based on the sum by weight of the two stated diols.

Especially suitable C11 diol mixtures comprise 2-pentyl-2-propyl-1,3-propanediol and 2-(2-methylbutyl)-2-propyl-1,3-propanediol in a weight ratio of approximately 8 to 12:1, i.e., from 8 to 12 times the amount, more particularly approximately 10 times the amount of 2-pentyl-2-propyl-1,3-propanediol in comparison to 2-(2-methylbutyl)-2-propyl-1,3-propanediol.

The C11 diol mixture may comprise further constituents; the amounts by weight above are intended only to define the weight ratio of the two diols to one another.

The Preparation of the C11 Diol or C11 Diol Mixture

2-Pentyl-2-propyl-1,3-propanediol and/or 2-(2-methylbutyl)-2-propyl-1,3-propanediol may be prepared by processes of the prior art.

In the case of the C11 diol mixture, the two diols may, for example, be synthesized individually and then mixed in the desired proportions or else used independently, without prior mixing, for preparing the polymers; in the case of the C11 diol mixture it is essential that the polymer comprises both dos in the corresponding amounts.

Preferably the C11 diol mixture is prepared as a mixture beforehand and used as a mixture for preparing the polymers.

Described below is one preferred synthesis pathway for the C11 diol mixture. From the C11 diol mixture it is possible to separate off the desired diols and so, if desired, to obtain 2-pentyl-2-propyl-1,3-propanediol and/or 2-(2-methylbutyl)-2-propyl-1,3-propanediol in pure form or to prepare any desired mixtures of these two diols.

WO 03/018192 describes the preparation of a C10 mixture which comprises 2-propylheptenal and 2-propyl-4-methylhexenal (e.g., in amounts of approximately 10:1) (steps a) to c) of the process claimed). Hydroformylation of butene gives a mixture of pentanal (n-valeraldehyde) and, in smaller amounts, 2-methylbutanal. Subsequent aldol condensation and water elimination produce a mixture of 2-propylheptenal and 2-propyl-4-methylhexenal.

The resulting mixture of 2-propylheptenal and 2-propyl-4-methylhexenal can be hydrogenated in a first process step to the corresponding alkanals (2-propylheptanal and 2-propyl-4-methylhexanal). The hydrogenation may be carried out in a customary way. A suitable hydrogenation process is described in DE-A 19524971, for example.

Preference is given to a catalytic hydrogenation using customary hydrogenation catalysts, e.g., palladium/$Al_2O_3$.

For the hydrogenation it is possible, for example, also to use nickel, copper, copper/nickel, copper/chromium, copper/chromium/nickel, zinc/chromium, and nickel/molybdenum catalysts. The catalysts may be unsupported, or the actively hydrogenating substances and/or their precursors may be applied to supports, such as $SiO_2$ or $Al_2O_3$, for example. The hydrogenation is preferably a liquid-phase hydrogenation. The hydrogenation can be carried out under a pressure of 1 to 100 bar. The reaction temperatures are situated preferably in the range of 50-200° C., preferably at 80 to 150° C.

The mixture of 2-propylheptanal and 2-propyl-4-methylhexanal obtained after the hydrogenation can be reacted by a crossed Cannizzaro reaction (Cannizzaro reaction using two different aldehydes; in this case aldehyde 1: the above mixture, and aldehyde 2: formaldehyde). The implementation of a crossed Cannizzaro reaction of this kind is familiar to the skilled worker and described in JP-HEI 03-161452, for example. As a catalyst it is preferred to use an alkali metal hydroxide (e.g., NaOH, $Ca(OH)_2$, KOH). The crossed Cannizzaro reaction is accompanied by formation of formic acid, which is produced as a salt (e.g., sodium formate or potassium formate) and can easily be separated off.

Another synthesis pathway instead of the crossed Cannizzaro reaction is, for example, the aldol reaction of 2-propylheptenal and 2-propyl-4-methylhexenal with formaldehyde and subsequent hydrogenation to the C11 diol mixture, as described in WO 04/092097, for example.

In all of its stages the process above can be carried out discontinuously or, preferably, continuously.

Particular preference is given to a C11 diol mixture which is obtainable by the above process, namely by
a) hydroformylation of butene to pentanal and 2-methylbutanal,
b) subsequent aldol reaction, with elimination of water, to 2-propylheptanal and 2-propyl-4-methylhexenal,
c) subsequent hydrogenation to 2-propylheptanal and 2-propyl-4-methylhexanal, and
d) crossed Cannizzaro reaction of 2-propylheptanal and 2-propyl-4-methylhexanal and formaldehyde or, alternatively, aldol reaction of 2-propylheptenal and 2-propyl-4-methylhexenal with formaldehyde and subsequent hydrogenation.

The resulting C11 diol mixture may if desired also comprise further constituents, more particularly other diols or aldehydes as well.

The resulting C11 diol mixture is generally composed of at least 90% by weight of the two diols of the formula I and II.

From the mixture obtained it is possible to separate off individual diols by distillation or to alter and tailor the concentration of the individual diols.

If alkoxylated diols are desired, an alkoxylation of the hydroxyl groups with alkylene oxides, such as ethylene oxide or propylene oxide, may be carried out subsequently.

The Polymers

The polymers are obtainable by polycondensation or polyaddition of monomeric compounds with accompanying use of the C11 diol or the C11 diol mixture; the polymers can, if desired, be modified chemically—functionalized or crosslinked, for example—by other or further reactions.

A polycondensation of monomeric compounds entails elimination of water or alcohol; a polyaddition does not entail any elimination.

Preferred polycondensates are polyesters, which are obtainable by reacting diols or polyols with dicarboxylic or polycarboxylic acids, which can also be used in the form of reactive derivatives, such as anhydrides or esters.

The term "polyesters" is intended below to refer to a polymer which is composed to an extent of more than 50%, more preferably of more than 70%, and more particularly of more then 90% by weight of synthesis components selected from diols, polyols, dicarboxylic acids, and polycarboxylic acids.

Mention may also be made of polycarbonate diols, which are obtainable by reacting dialkyl carbonates with diols, with elimination of alcohols.

A particular polyadduct that may be mentioned is polyurethane. Also suitable, for example, are polyadducts obtainable by ring-opening polymerization of lactones or lactams.

The term "polyurethane" is intended below to refer to a polymer which is composed of more than 50%, more preferably of more than 70%, and more particularly of more than 90% by weight of synthesis components selected from diisocyanates, polyisocyanates, diols, and polyols.

A feature common to all of these polymers is that they are synthesized substantially from diols and from compounds that are reactive with these diols, such as di- and/or polycarboxylic acids (polyesters) or di- and/or polyisocyanates (polyurethanes).

Preferred polymers are polyesters and polyurethanes; polyesters are particularly preferred.

The polymers of the invention preferably have the content indicated below for the C11 diol or for the C11 diol mixture; the weight figures below relating to the amount of the C11 diol or C11 diol mixture in the polymer refer to the units of the polymer that derive from the C11 diol or C11 diol mixture. In the case of polyadducts the weight of these units corresponds unchanged to the C11 diol or C11 diol mixture; in the case of polycondensates the weight of these units is reduced by the hydrogen atoms of the hydroxyl groups.

Preferred polymers are composed to an extent of at least 0.5%, more preferably at least 2%, very preferably at least 5%, and more particularly at least 10% by weight, and in one particular embodiment at least 20% by weight, of the C11 diol or the C11 diol mixture. Since the accompanying use of other compounds reactive with the diols is mandatory, the polymers are generally composed to an extent of not more than 70%, more particularly not more than 60%, or not more than 50% by weight of the C11 diol or the C11 dial mixture.

Besides the C11 diol or C11 diol mixture the polymers may also comprise other diols or polyols as synthesis components. In one preferred embodiment at least 10%, more preferably at least 25%, and very preferably at least 50% by weight of the diols and polyols of which the polymers are composed is accounted for by the C11 diol or the C11 diol mixture.

More particularly at least 70% or at least 90% by weight of the diols and polyols of which the polymers are composed may be the C11 diol or the C11 diol mixture.

In one particular embodiment 100% by weight of all of the diols and polyols of which the polymers are composed may be the C11 diol or the C11 diol mixture.

Further Constituents of the Polyesters

Besides the C11 diol or C11 diol mixture, polyesters may comprise further diols or polyols as synthesis components.

Examples of diols include ethylene glycol, propylene glycol, and their more highly condensed counterparts, such as diethylene glycol, triethylene glycol, dipropylene glycol, tripropylene glycol, etc., butanediol, pentanediol, hexanediol, neopentylglycol, alkoxylated phenolic compounds, such as ethoxylated and/or propoxylated bisphenols, and cyclohexanedimethanol; polyols suitable as a further synthesis component are trifunctional and higher polyfunctional alcohols, such as glycerol, trimethylolpropane, butanetriol, trimethylolethane, pentaerythritol, neopentylglycol, ditrimethylolpropane, dipentaerythritol, sorbitol, and mannitol.

The above diols or polyols may be alkoxylated, more particularly ethoxylated and propoxylated. The alkoxylation products are obtainable in a known way by reaction of the above alcohols with alkylene oxides, more particularly ethylene oxide or propylene oxide. The degree of alkoxylation per hydroxyl group is preferably 0 to 10, i.e., 1 mol of hydroxyl group may be alkoxylated preferably with up to 10 mol of alkylene oxides.

The polyesters further comprise dicarboxylic or polycarboxylic acids as synthesis components. In preparing the polyesters, dicarboxylic or polycarboxylic acids may also be used in the form of their reactive derivatives, as anhydrides or esters, for example. Suitable dicarboxylic acids are succinic acid, glutaric acid, adipic acid, sebaccic acid, isophthalic acid, terephthalic acid, their isomers and hydrogenation products, such as tetrahydrophthalic acid. Also suitable are maleic acid and fumaric acid for unsaturated polyesters.

Polyesters may also comprise monoalcohols or monocarboxylic acids as constituents; using such compounds as accompaniments allows the molecular weight to be adjusted and/or limited.

In order to achieve particular properties, the polyesters may comprise particular functional groups. Water-soluble or water-dispersible polyesters comprise the necessary amount of hydrophilic groups, carboxyl groups or carboxylate groups, for example, to achieve solubility or dispersibility in water. Crosslinkable polyesters, for powder coating materials, for example, comprise functional groups which enter into a crosslinking reaction with the crosslinking agent used. These may likewise be carboxylic acid groups, if crosslinking is intended with compounds comprising hydroxyl groups, hydroxyalkylamides, for example. The functional groups may also be ethylenically unsaturated groups, as a result, for example, of modification of the polyester with unsaturated dicarboxylic acids (maleic acid) or reaction with (meth) acrylic acid; polyesters of this kind are radiation-curable.

Unsaturated polyesters may also be copolymerized with monoethylenically unsaturated or else polyethylenically unsaturated, free-radically polymerizable compounds, such as styrene, C1-C10 alkyl acrylates, dialkyl acrylates, such as the diacrylate of ethanediol or butanediol, for example. The unsaturated polyester may for this purpose be used in a mixture with the ethylenically unsaturated monomers, as is described in WO 00/23495 and EP 1131372, for example. In this case the above ethylenically unsaturated compounds serve simultaneously as solvents (reactive diluents), and so the mixture is present preferably as a solution of the polyesters in these compounds.

The mixture may be used, for example, as a coating or impregnating composition, not least for the production of laminates. Curing may take place thermally or photochemically, in both cases also if desired with addition of an initiator.

Further Constituents of the Polyurethanes

Polyurethanes comprise di- or polyisocyanates as an essential synthesis component.

Included in particular are diisocyanates X(NCO)2, where X is an aliphatic hydrocarbon radical having 4 to 15 carbon atoms, a cycloaliphatic or aromatic hydrocarbon radical having 6 to 15 carbon atoms or an araliphatic hydrocarbon radical having 7 to 15 carbon atoms. Examples of such diisocyanates are tetramethylene diisocyanate, hexamethylene diisocyanate, dodecamethyene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl) propane, trimethylhexane diisocyanate, 1,4-diisocyanatobenzene, 2,4-diisocyanatotoluene, 2,6-diisocyanatotoluene, 4,4-diisocyanatodiphenylmethane, 2,4'-diisocyanatodiphenylmethane, p-xylylene diisocyanate, tetramethylxylylene diisocyanate (TMXDI), the isomers of bis(4-isocyanatocyclohexyl)methane (HMDI) such as the trans/trans, the cis/cis, and the cis/trans isomers, and mixtures of these compounds.

Diisocyanates of this kind are available commercially.

Particularly significant mixtures of these isocyanates are the mixtures of the respective structural isomers of diisocyanatotoluene and diisocyanatodiphenylmethane; particularly suitable is the mixture of 80 mol % 2,4-diisocyanatotoluene and 20 mol % 2,6-diisocyanatotoluene. Also advantageous in particular are the mixtures of aromatic isocyanates such as 2,4-diisocyanatotoluene and/or 2,6-diisocyanatotoluene with aliphatic or cycloaliphatic isocyanates such as hexamethylene diisocyanate or IPDI, the preferred mixing ratio of aliphatic to aromatic isocyanates being 4:1 to 1:4.

As diols and/or polyols which are reacted with the di- or polyisocyanates, use is made in accordance with the invention of the C11 dial alone or the C11 diol in a mixture with other diols or polyols.

In the case of polyurethanes, the dials used preferably include polyesterols, in particular polyester dials. Such polyesterols are obtained beforehand by reaction of diols or polyols with dicarboxylic or polycarboxylic acids (see description of the polyesters above). The C11 diol may be present in the polyurethanes in the form of such polyesterols. Further diols and polyols include those identified above, whether as synthesis components which are reacted directly with the di- or polyisocyanates or else as a constituent of the polyester diols. Suitable dicarboxylic or polycarboxylic acids for the polyester dials are likewise those specified above.

The polyurethanes may also comprise monoalcohol or monoisocyanate constituents; by using such compounds in accompaniment it is possible to adjust or limit the molecular weight.

In order to achieve particular properties, the polyurethanes may comprise particular functional groups. Water-soluble or water-dispersible polyurethanes comprise the necessary amount of hydrophilic groups, carboxyl groups or carboxylate groups, for example, for achieving solubility or dispersibility in water. An example of a suitable synthesis component is dimethylolpropionic acid. Crosslinkable polyurethanes comprise functional groups which enter into a crosslinking reaction with the crosslinking agent used. Besides urethane groups, the polyurethanes may also comprise, in particular, other functional groups, urea groups, for example, which come about through reaction of the di- or polyisocyanates with amino compounds.

The polymers can if desired be modified chemically—functionalized or crosslinked, for example—by other or further reactions, during or else, in particular, at a later point in time, as on their use, for example.

More particularly the polymers may comprise crosslinking groups which enter into a crosslinking reaction as soon as the necessary conditions are present. The polymers may in particular also be used in a mixture with crosslinkers which enter into a crosslinking reaction with the polymer at the desired point in time under the necessary conditions (more particularly at elevated temperature).

According to the reactivity of the crosslinkers, a distinction is made between one-component (1C) and two-component (2C) systems. In 2C systems, the crosslinker is not added until shortly before the subsequent use; in the case of 1C systems, the crosslinker can be added to the system at an early stage (latent crosslinker), and crosslinking takes place only in the case of the subsequently set conditions, such as when solvent is removed and/or temperature increased, for example.

Examples of customary crosslinkers include isocyanates, epoxides, acid anhydrides or else, in the case of polymers with free-radically polymerizable, ethylenically unsaturated groups, ethylenically unsaturated monomers such as styrene.

The Use of the Polymers

The polymers are suitable as constituents of thermoplastic compositions. For this purpose the polymers, polyesters or polyurethanes, for example, preferably have a sufficiently high molecular weight to give them thermoplastic properties.

Thermoplastic compositions are used in general for producing moldings, in which case customary methods such as injection molding, extrusion or blow molding may be employed.

In particular the polymers are suitable as a constituent of coating compositions, sealants or adhesives.

The coating compositions, sealants or adhesives comprise the polymers of the invention preferably as binders. They may comprise further binders and other additives, examples being antioxidants, stabilizers, dyes, pigments, flow control assistants, thickeners or wetting assistants.

The coating compositions, sealants or adhesives may be aqueous or solvent borne compositions. Aqueous compositions are preferred.

Compositions of this kind comprise the binders of the invention preferably in the form of solutions or dispersions in water or organic solvents or mixtures thereof. Where necessary the polymers comprise additional functional groups which bring about solubility or dispersibility in water or organic solvents, preferably in water (see above).

The coating compositions, sealants or adhesives may also be compositions which are largely free of water or organic solvents (and are known as 100% systems).

Compositions of this kind generally comprise less than 10 parts by weight of water or other organic solvents (boiling point less than 150° C. at 1 bar) per 100 parts by weight of the compositions. With particular preference they comprise less than 2 parts, with very particular preference less than 1 part, or less than 0.5 part by weight of water or other organic solvents (boiling point less than 150° C. at 1 bar) per 100 parts by weight of the compositions.

The compositions in question may still be fluid at room temperature or may be compositions in powder form, for example, which are processed only at elevated temperatures.

The compositions, coating compositions more particularly, may be radiation-curable and/or be used as radiation-curable compositions or coating compositions. For that purpose they preferably comprise a radiation-curable polymer of the invention, more particularly a radiation-curable polyester (see above). Radiation curing may take place using high-energy radiation, for example, electron beams or UV light; when UV light is used it is possible with preference to add a photoinitiator to the polymers.

One preferred use in the context of the present invention is the use of the polymers of the invention as or in powder coating materials. It is preferred to use polyesters as powder coating material which are crosslinkable.

In one preferred embodiment the powder coating material is produced by mixing and melting the polyester, crosslinker, and further additives, pigments and flow control agents, for example, at high temperatures. The mixture can be brought into the powder form by subsequent extrusion and corresponding processing of the extrudate.

The powder coating material may be coated onto the desired substrates, examples being those with surfaces of metal, of plastic or of wood, in a customary way, including, for example, electrostatically.

The polymers of the invention have a low viscosity, and also a low melt viscosity (100% systems) or a low solution viscosity (polymer solutions). The low viscosity permits ease of handling, results in good coating properties, and permits higher solids fractions in solutions or dispersions or lower binder fractions in pigmented compositions. The polymers of the invention are also in particular very resistant to hydrolysis.

In the context of their use in coating compositions, sealants, and adhesives, the polymers of the invention produce good mechanical properties; in particular, the coating compositions, powder coating materials for example, have high impact toughness, good elasticity, and good gloss.

EXAMPLES

Preparation of the C11 Diol Mixture
Selective hydrogenation of 2-propylheptenal:2-propyl-4-methylhexenal:

The starling solution was an isomer mixture including 2-propylheptenal and 2-propyl-4-methylhexenal (~10:1), which was prepared from a C5 aldehydes isomer mixture, as described in WO 2003 018192 A1.

The mixture was run as a hydrogenation feed (mixture comprised 91% by weight C10 aldehydes) in trickle mode with an $H_2$ pressure of 40 bar in a reactor heated to 105° C. (14 l fixed-bed reactor, 70 mm diameter). The space velocity was 0.1 $kg_{organic}/l_{CAT}$*h. Part of the hydrogenation discharge was mixed back into the feed (circulation mode). The ratio of circulation to feed was 10:1. A feed of 1.3 kg/h and 500 Nl/h of fresh gas were run into the reactor. The discharge included 10.7% of 2-propyl-4-methylhexanal, 78.7% of 2-propylheptanal, and 2% of C10 alcohols.

Crossed Cannizzaro Reaction

A 5000 ml HWS reaction flask with cooled reflux condenser, liquid receiver, cryostat, and KPG stirrer was charged with 865 g of a mixture of 2-propylheptanal and 2-propyl-4-methylhexanal (mixture comprised 87% of 010 saturated aldehydes), 1500 g of formaldehyde (30% strength in water), and 238 g of methanol. Over a period of 3 hours at 50° C., 1.273 g of 25% strength NaOH were added dropwise using a HPLC pump. The batch was stirred at 55° C. for a further 1 h. Following cooling to room temperature, the pH was adjusted with formic acid. The phases were separated and the organic phase was freed from low boilers (20 mbar and 85° C.) and then distilled under reduced pressure through a packed column (250 mm long, 40 mm diameter). 780 g (83% yield) of a mixture (~10:1, 96%) of 2-propyl-2-(2-methylbutyl)-1,3- propanediol (93%) and 2-propyl-2-pentyl-1,3-propanediol (5.8%) were obtained. The main fraction was obtained at an overhead temperature of between 128-132° C. (liquid-phase temperature 152-165° C.) under a pressure of 1 mbar. The structure of the diols was determined by means of GC, GC-MS, and NMR ($^1$H, $^{13}$C).

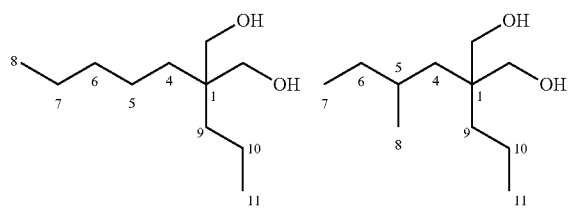

Chemical shifts in $^{13}$C NMR for the principal isomers (DMSO): 2-propyl-2-pentyl-1,3-propanediol δ (ppm)=64.1 (2×CH$_2$OH), 21.9 (C$_5$), 22.2 (C$_7$), 32.5 (C$_9$), 14.9 (C$_{11}$), 41.1 (C$_1$), 30.4 (C$_4$), 33.0 (C$_6$), 13.83 (C$_8$) 15.6 (C$_{10}$); 2-propyl-2-(2-methylbutyl)-1,3-propanediol δ (ppm)=69.5 (2×CH$_2$OH), 29.2 (C$_5$), 11.3 (C$_7$), 29.7 (C$_9$), 14.9 (C$_{11}$), 36.9 (C$_1$), 45.1 (C$_4$), 31.0 (C$_6$), 22.0 (C$_8$), 15.6 (C$_{10}$).

Preparation of an ~50:50 mixture of 2-propyl-2-(2-methylbutyl)-1,3-propanediol and 2-propyl-2-pentyl-1,3-propanediol A C11 diol mixture (10:90 2-propyl-2-(2-methylbutyl)-1,3-propanediol and 2-propyl-2-pentyl-1,3-propanediol) was distilled in a packed column (2 m long). Under a pressure of 1 mbar and with an overhead temperature of between 120-122° C. (liquid-phase temperature 172-178° C.), a 50:50 mixture of the dials was obtained. The ratio of the diols was determined by means of GC and NMR.

Preparation of pure 2-propyl-2-pentyl-1,3-propanediol (purity 96 GC area %)

This diol was obtained by distilling a main fraction of the C11 diol mixture (~10:90 2-propyl-2-(2-methylbutyl)-1,3-propanediol and 2-propyl-2-pentyl-1,3-propanediol) on a packed column (2 m long). The pure 2-propyl-2-pentyl-1,3-propanediol was obtained under a pressure of 1 mbar and at an overhead temperature of 123° C. (175-81° C.). The purity and structure were determined by means of GC and NMR.

Use Examples

Examples

Abbreviations
ADA: adipic acid
D: polydispersity index (M$_w$/M$_n$)
DPG: dipropylene glycol
DBTO: dibutyltin oxide
DSC: differential scanning calorimetry
GPC: gel permeation chromatography
IPA: isophthalic acid
M$_n$: number-average molecular weight in [g/mol]
M$_w$: weight-average molecular weight in [g/mol]
NVC: nonvolatiles content
NPG: neopentyl glycol
OHN: OH number
C11 diol mixture: mixture of 2-pentyl-2-propyl-1,3-propanediol and 2-(2-methylbutyl)-2-propyl-1,3-propanediol (formulae I and II above) in 10:1 weight ratio
PPPD: 2-pentyl-2-propyl-1,2-propanediol AN: acid number
T$_g$: glass transition temperature
TMP: trimethylolpropane
TMAA: trimellitic anhydride
TPA: terephthalic acid
η$_1$: melt viscosity
η$_2$: solution viscosity Methods of Polymer Characterization The molecular weight determinations are carried out by GPC. Stationary phase: highly crosslinked porous polystyrene-divinylbenzene, available commercially as PL-GEL from Polymer Laboratories. Mobile phase: THF. Flow rate: 0.3 ml/min. Calibration with polyethylene glycol 28700 to 194 daltons from PSS.

The acid number of the polyesters is determined by the DIN standard method 53169. The melt viscosity η$_1$ of the polyesters is determined using a cone/plate viscometer at 160° C. in oscillation mode and with an angular velocity of 0.1 rad/s. The solution viscosity η$_2$ of the polyesters is determined using a cone/plate viscometer at room temperature in rotation mode. The solutions are composed of 70% polyester and 30% solvent (5/1 mixture of Solvesso 100™/Solvenon PM™).

The Tg of the polyesters is determined by means of DSC in accordance with ASTM D3418.

Preparation of Powder Polyesters with COOH Groups
Polyester P1
Stage 1—Preparation of the OH-Containing Oligomer 149.1 g of C11 diol mixture (0.80 mol). 266.7 g of NPG (2.56 mol), 53.7 g of TMP (0.4 mol), 532.1 g of TPA (3.21 mol), and 0.7 g of DBTO catalyst are charged to a 2 L four-neck flask equipped with thermometer, inert gas inlet, stirrer, and reflux condenser. With a stream of nitrogen being passed through, and under reflux, the mixture of reactants is heated rapidly to 180° C. Water is distilled off continuously. Subsequently the reaction mixture is heated in stages to 230° C. over the course of 3 to 5 hours, with stirring and with a flow of nitrogen, and is stirred further at 230° C. until the oligomer has a AN of 10 to 15 mg KOH/g. The AN of the oligomer is 10 mg KOH/g.

Stage II—Preparation of the COOH-Containing Polymer P1

The oligomer synthesized above is cooled to 180° C. and then 133.0 g of IPA (0.80 mol) are added. The temperature is raised to 230° C. and condensation is continued under these conditions until the polymer has an AN of 30 to 40 mg KOH/g. The water produced from the polymerization can be stripped off at the end of the reaction by a gentle vacuum, in order to give the desired AN. The product is a branched, COOH-containing powder polyester P1 whose AN is 30 mg KOH/g. P1 has a glass transition temperature T$_g$ of 66° C. and a melt viscosity η$_1$ of 327 Pa·s at 160° C. GPC analysis yields the following values: M$_n$=2980 g/mol D=19.4 (see Table 1).

Polyesters P2 to P7

The procedure for the preparation of P1 is repeated, with the compositions summarized in Table 1. The products are branched, COOH-containing powder polyesters whose key AN, M$_n$, D, T$_g$, and η$_1$ data are listed in Table 1.

P2 for comparison
P3
P4
P5 for comparison
P6
P7 for comparison

TABLE 1

| Polyester | Composition | | | | | Key polyester data | | | | |
|---|---|---|---|---|---|---|---|---|---|---|
| | C11 diol mixture [g] | NPG [g] | TMP [g] | TPA [g] | IPA [g] | AN [mg KOH/g] | $M_n$ [g/mol] | D | $T_g$ [°C.] | $\eta_1$ [Pa·s] |
| P1 | 149.1 | 266.7 | 53.7 | 532.1 | 133.0 | 30 | 280 | 19.4 | 66 | 327 |
| P2 | 0 | 374.9 | 57.5 | 570.0 | 142.5 | 36 | 2430 | 76.1 | 76 | 4660 |
| P3 | 152.2 | 283.9 | 15.8 | 475.5 | 203.8 | 57 | 1630 | 2.7 | 59 | 12.3 |
| P4 | 152.2 | 283.9 | 15.8 | 475.5 | 203.8 | 46 | 2270 | 3.3 | 67 | 41.5 |
| P5 | 0 | 396.0 | 17.0 | 510.3 | 218.7 | 57 | 1890 | 3.6 | 69 | 52.7 |
| P6 | 151.0 | 295.9 | 13.6 | 472.1 | 202.3 | 38 | 2525 | 3.5 | 67 | 42.8 |
| P7 | 0 | 407.9 | 14.6 | 506.1 | 216.9 | 38 | 2400 | 3.2 | 73 | 53.6 |

The inventive polymers P1, P3 and P6 have a significantly lower melt viscosity than the corresponding comparative polymers P2, P5 and P7.

Comparative Example Polyester P8

The same procedure as for the preparation of P1 is carried out, with the composition summarized in Table 2. Polyester contains no C11 diol mixture, but instead the linear PPPD.

TABLE 2

| Polyester | Composition | | | | | Key polyester data | | | | |
|---|---|---|---|---|---|---|---|---|---|---|
| | PPPD [g] | NPG [g] | TMP [g] | TPA [g] | IPA [g] | SZ [mg KOH/g] | $M_n$ [g/mol] | D | $T_g$ [°C.] | $\eta_1$ [Pa·s] |
| P8 | 152.2 | 283.9 | 15.8 | 475.5 | 203.8 | 55 | 1940 | 3.3 | 66 | 33.6 |

The inventive C11 diol mixture-containing polymer P3 (Table 1) has a lower melt viscosity than the corresponding PPPD-containing comparative polymer P8.

Preparation of Amorphous Polyesters with OH Groups

Polyester P9

206.25 g of C11 diol mixture (1.11 mol), 182.98 g of NPG (1.76 mol), 148.59 g of TMP (1.11 mol), 429.50 g of IPA (2.59 mol), 161.90 g of ADA (1.11 mol), and 0.5 g of DBTO catalyst are charged to a 2 L four-neck flask equipped with thermometer, inert gas inlet, stirrer, and reflux condenser. With a stream of nitrogen being passed through, and under reflux, the mixture of reactants is heated rapidly to 160° C. Water is distilled off continuously. Subsequently the reaction mixture is heated in stages to 230° C. over the course of 3 to 5 hours, with stirring and with a flow of nitrogen, and is stirred further at 230° C. until the polyester P8 has an AN of 10 to 15 mg KOH/g. The product is branched, amorphous, OH-containing polyester P8 whose AN is 14 mg KOH/g. P8 has an OHN of 82 mg KOH/g and a glass transition temperature $T_g$ of 19° C. GPC analysis yields the following values: $M_n$=2000 g/mol; D=5.3. P8 has a melt viscosity $\eta_1$ of 1.3 Pa·s at 160° C. The solution viscosity $\eta_2$ of the polyester P8 at room temperature (P8 solution with 70% NVC and a 5/1 mixture of Solvesso 100™/Solvenon PM™ as solvent) is 12.1 Pa·s (see Table 3).

Polyester P10 (for Comparison)

The same procedure as for the preparation of P9 is carried out, with the composition summarized in Table 3. The key data of the polyester P10 are listed in Table 3.

TABLE 3

| Polyester | Composition | | | | | | Key polyester data | | | | | | |
|---|---|---|---|---|---|---|---|---|---|---|---|---|---|
| | C11 diol mixture [g] | NPG [g] | TMP [g] | IPA [g] | ADA [g] | | AN [mg KOH/g] | OHN [mg KOH/g] | $M_n$ [g/mol] | D | $T_g$ [°C.] | $\eta_1$ [Pa·s] | $\eta_2$ [Pa·s] |
| P9 | 206.3 | 183.0 | 148.6 | 429.5 | 161.9 | | 14 | 82 | 2000 | 5.3 | 19 | 1.3 | 12.1 |
| P10 | 0 | 326.6 | 163.9 | 473.9 | 178.6 | | 15 | 108 | 2195 | 16.8 | 25 | 6.3 | 41.6 |

The inventive polymer P9 has a significantly lower melt viscosity and a significantly lower solution viscosity than the comparative polymer P10.

Preparation of Water-Dilutable Polyesters

Polyester P11

Stage 1—Preparation of the OH-Containing Oligomer 242.8 g of C11 diol mixture (1.29 mol), 302.2 g of NPG (2.91 mol), 401.9 g of IPA (2.42 mol), and 0.5 g of DBTO catalyst are charged to a 2 L four-neck flask equipped with thermometer, inert gas inlet, stirrer, and reflux condenser.

With a stream of nitrogen being passed through, and under reflux, the mixture of reactants is heated rapidly to 160° C. Water is distilled off continuously. Subsequently the reaction mixture is heated in stages to 220° C. over the course of 3 to 5 hours, with stirring and with a flow of nitrogen, and is stirred further at 220° C. until the reaction mixture has an AN of 10 to 15 mg KOH/g. The AN of the oligomer is 15 mg KOH/g.

Stage II—Preparation of the Polymer P11

The oligomer synthesized above is cooled to 160° C. and then 155.0 g of TMAA (0.81 mol) are added. The temperature is raised to 230° C. and condensation is continued under these conditions until the polymer has an AN of 42 to 48 mg KOH/g. The water produced from the polymerization can be stripped off at the end of the reaction by a gentle vacuum, in order to give the desired AN. The product is a linear, water-dilutable polyester P11 whose AN is 46 mg KOH/g. P11 has a glass transition temperature $T_g$ of 41° C. and a melt viscosity $\eta_1$ of 1.4 Pa·s at 160° C. GPC analysis yields the following values: $M_n$=1200 g/mo; D=1.9 (see Table 4).

Assessment of Hydrolysis Resistance of P11

A 20% strength aqueous colloidal solution of P11 is prepared, brought to pH of 8 using N,N-dimethylethanolamine, and stored at 45° C. The time interval taken for the colloidal solution to precipitate is taken as a measure of the hydrolysis resistance of the polyester (see Table 5).

Polyester P12 (for Comparison)

The same procedure as for the preparation of P11 is carried out, with the composition summarized in Table 4. The key data of the polyester P12 are listed in Table 4.

Preparation of Powder Coating Materials

As a reference binder (REF) the polyester resin Uralac® P-862 from DSM Resins B.V. is utilized ($T_g$ 58.0° C., AN 35 mg KOH/g). Powder coating materials PL3, PL4, PL5, and PLR are prepared by mixing, correspondingly, 570.0 g of powder polyesters P3, P4, P5 (for comparison) or REF in each case with 30.0 g of commercial curing agent Primid® XL-552 (hydroxyalkylamide from DSM), 300.0 g of titanium dioxide pigment Kronos® 2160 (from Kronos), 9.0 g of flow control agent Resiflow® PV5 (from Worlée Chemie GmbH), and 2.5 g of degassing agent, benzoin, in a universal laboratory mixer (from MIT Mischtechnik GmbH), melting the mixture and subsequently extruding the melt from a twin-screw extruder (MP 19, APV) at 80-100° C. The resulting extrudate is then coarsely crushed, ground and sieved. The resulting powder coating materials PL3, PL4, and PL5 are subjected to the following tests:

| Test parameter | Test method |
| --- | --- |
| Flow properties | Fluidizability DIN ISO 8130-5 |
|  | Tableting DIN ISO 8130-11 |
| Gel time | DIN ISO 8130-6 |

Thereafter the powder coating materials are applied electrostatically to steel test panels (Q-Panel R-36) which are baked at 160° C. for 10 minutes. The aim is to obtain coat

TABLE 4

| Polyester | Composition | | | | Key polyester data | | | | | |
| --- | --- | --- | --- | --- | --- | --- | --- | --- | --- | --- |
|  | C11 diol mixture [g] | NPG [g] | IPA [g] | TMMA [g] | AN [mg KOH/g] | OHN [mg KOH/g] | $M_n$ [g/mol] | D | $T_g$ [° C.] | $\eta_1$ [Pa·s] |
| P11 | 242.8 | 302.2 | 401.9 | 155.0 | 46 | 57 | 1200 | 1.9 | 41 | 1.4 |
| P12 | 0 | 490.4 | 451.6 | 174.1 | 47 | 58 | 1250 | 2.3 | 51 | 3.7 |

The inventive polymer P11 has a significantly lower melt viscosity than the comparative polymer P12.

TABLE 5

| Polyester | Time to precipitation of the aqueous solution (days) |
| --- | --- |
| P11 | >30 days |
| P12 | 17 days |

The inventive polymer P11 is significantly more resistant to hydrolysis than the comparative polymer P12.

thicknesses of 60 µm to 80 µm. The resulting coatings are subjected to the following tests:

| Test parameter | Test method |
| --- | --- |
| Appearance | Visual assessment of the surfaces |
| Gloss | DIN EN ISO 2813 |
| Impact toughness | EN ISO 6272 |
| Impact sensitivity | ASTM D 2794 |
| Elasticity | EN ISO 1520 |
| Weather stability | Accelerated weathering test (QUV-A) DIN EN ISO 11507 |

The results of the coatings tests are summarized in Table 6.

TABLE 6

| | Test parameter | Test method | PL3 | PL4 | PL5 (comparative) | PLR (comparative) |
| --- | --- | --- | --- | --- | --- | --- |
| Powder coating material | Flow properties | Fluidizability | 117.8 | 154.1 | 160.4 | 124.6 |
|  | Gel time | Tableting @ 180° C. [mm] | 22.2 | 18.8 | 13.5 | 30.5 |
|  |  |  | 195 | 154 | 154 | 173 |
|  |  | Gel time @ 180° C. [s] |  |  |  |  |
| Metal test panels | Appearance | Visual assessment | 2* | 1** | 2 | 2 |
|  | Gloss | Gloss measurement at 20° | 81 | 79 | 75 | 63 |
|  | Impact toughness | Reverse impact [kg * cm] | 20 | 80 | 50 | 200 |
|  | Impact sensitivity | Impact [kg * cm] | 160 | 200 | 80 | 200 |
|  | Elasticity | Erichsen cupping [mm] | 8.1 | 10.2 | 10.1 | 10.6 |

TABLE 6-continued

| Test parameter | Test method | PL3 | PL4 | PL5 (comparative) | PLR (comparative) |
|---|---|---|---|---|---|
| Weathering stability | Residual gloss after 1000 h QUV-A [%] | 82 | 86 | 84 | 88 |

*2 = Orange peel, pinholes
**1 = Orange peel, individual pinholes

The powder coating materials of the invention have very good performance properties. PL3 and PL4 have a better gloss, and PL4 better mechanical properties, than PL5.

Preparation of High-Solids 1-Component (1K) Coating Materials

For preparing the high-solids 1K coating materials 1K-PL9 and 1K-PL10, 70% strength solutions of the polyesters P9 and P10 in butyl acetate are prepared correspondingly. 80 g of each of the 70% strength polyester solutions are mixed with 14 g of commercial curing agent Luwipal® 066 (melamine condensate from BASF), 4 g of n-butanol, and 2 g of p-toluene sulfonic acid catalyst. The resulting solutions (NVC 70%) are applied to glass plates and steel test panels using a four-way bar applicator. The target film thicknesses are from 40 µm to 50 µm. The coated test panels are subsequently baked at 140° C. for 30 minutes. The resulting coatings are subjected to the following tests:

|  | Test parameter | Test method |
|---|---|---|
| Glass plates | Appearance | Visual assessment of the surfaces |
|  | Gloss | DIN EN ISO 2813 |
|  | Impact sensitivity | DIN 53157 |
| Steel test panels | Impact sensitivity | DIN 53157 |
|  | Elasticity | DIN 53156 |
|  | Hydrolysis resistance | Daimler-Chrysler Test PBODCC371 |
|  | Chemical resistance | Daimler-Chrysler Test PBODCC371 |

The results of the coatings tests are summarized in Table 7. 1K-PL9 (based on polyester P9) is inventive, while 1K-PL10 (based on polyester P10) serves as a comparative example.

TABLE 7

|  | Test parameter | Test method | 1K-PL9 | 1K-PL10 |
|---|---|---|---|---|
| Glass plates | Appearance | Visual assessment | clear | clear |
|  | Gloss | Gloss measurement at 20° | 166 | 175 |
|  | Impact sensitivity | Pendulum damping (König) [seconds] | 220 | 232 |
|  |  | Pendulum damping [deflections] | 164 | 166 |
| Steel test panels | Impact sensitivity | Pendulum damping (König) [seconds] | 224 | 227 |
|  |  | Pendulum damping [deflections] | 160 | 164 |
|  | Elasticity | Erichsen cupping [mm] | 8.5 | 8.3 |
|  | Hydrolysis resistance | $T_{max}$ [° C.] - distilled water | 63 | 78 |
|  | Chemical resistance | $T_{max}$ [° C.] - pancreatin in water (50%) | 44 | 60 |
|  |  | $T_{max}$ [° C.] - sulfuric acid (1%) | 53 | 39 |
|  |  | $T_{max}$ [° C.] - sodium hydroxide (1%) | 43 | 53 |

The inventive high-solids coating material 1K-PL9 shows a very good profile of properties. In particular, the C11 diol mixture shows an advantage over NPG with respect to the elasticity of the film, and also the acid resistance.

Preparation of High-Solids 2-Component (2K) Coating Materials

For preparing the high-solids 2K coating materials 2K-PL9 and 2K-PL10, 70% strength solutions of the polyesters P9 and P10 in butyl acetate are prepared correspondingly. 70 g of each of the 70% strength polyester solutions are mixed with 1 g of a solution (10% strength in butyl acetate) of the flow control agent Baysilon® OL17 (polyether from Borchers GmbH), 1 g of dibutyltin dilaurete solution (5% strength in butyl acetate) as catalyst, 3 g of methoxypropyl acetate, 20 g of commercial curing agents Basonat® HI 190 BS (90% form, polyisocyanates from BASF), and 5 g of butyl acetate. The resulting solutions (NVC 67%) are applied to glass plates and steel test panels using a four-way bar applicator. The target film thicknesses are from 40 µm to 50 µm. The coated test panels are subsequently baked at 80° C. for 30 minutes. The resulting coatings are subjected to the following tests:

|  | Test parameter | Test method |
|---|---|---|
| Glass plates | Appearance | Visual assessment of the surfaces |
|  | Gloss | DIN EN ISO 2813 |
|  | Impact sensitivity | DIN 53157 |
| Steel test panels | Impact sensitivity | DIN 53157 |
|  | Elasticity | DIN 53156 |
|  | Hydrolysis resistance | Daimler-Chrysler Test PBODCC371 |
|  | Chemical resistance | Daimler-Chrysler Test PBODCC371 |

The results of the coatings tests are summarized in Table 8. 2K-PL9 (based on polyester P9) is inventive, while 2K-PL10 (based on polyester P10) serves as a comparative example.

TABLE 8

|  | Test parameter | Test method | 2K-PL9 | 2K-PL10 |
|---|---|---|---|---|
| Glass plates | Appearance | Visual assessment | clear | clear |
|  | Gloss | Gloss measurement at 20° | 163 | 166 |
|  | Impact sensitivity | Pendulum damping (König) [seconds] | 205 | 186 |
| Steel test panels | Impact sensitivity | Pendulum damping [deflections] | 146 | 134 |
|  |  | Pendulum damping (König) [seconds] | 213 | 186 |
|  |  | Pendulum damping [deflections] | 152 | 133 |
|  | Elasticity | Erichsen cupping [mm] | 10.4 | 10.3 |
|  | Hydrolysis resistance | $T_{max}$ [° C.] - distilled water | 50 | 55 |
|  | Chemical resistance | $T_{max}$ [° C.] - pancreatin in water (50%) | 39 | 39 |
|  |  | $T_{max}$ [° C.] - sulfuric acid (1%) | 49 | 50 |
|  |  | $T_{max}$ [° C.] - sodium hydroxide (1%) | 44 | 52 |

The inventive high-solids coating material 2K-PL9 shows a very good profile of properties. The mechanical properties are significantly better than for the coating material 2K-PL10 based on NPG.

The invention claimed is:

1. A polymer, obtained by polycondensation or polyaddition of at least one monomeric compound with 2-(2-methylbutyl)-2-propyl-1,3-propanediol of formula (I)

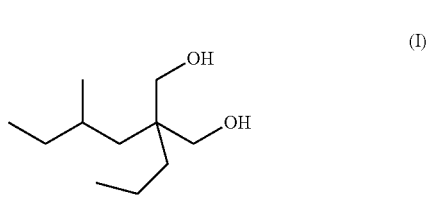

or (Ia) at least one alkoxylated derivative of 2-(2-methylbutyl)-2-propyl-1,3-propanediol, wherein the polymer is a polyester.

2. The polymer according to claim 1, wherein the polycondensation or polyaddition is with a mixture of 2-(2-methylbutyl)-2-propyl-1,3-propanediol or the at least one (Ia) alkoxylated derivative and 2-pentyl-2-propyl-1,3-propanediol of formula (II)

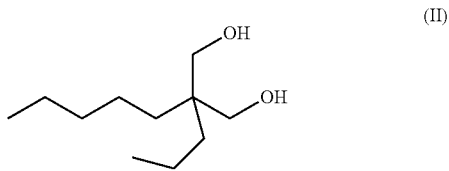

or (IIa) at least one alkoxylated derivative of 2-pentyl-2-propyl-1,3-propanediol.

3. The polymer according claim 2, wherein the mixture comprises:
1% to 99% by weight of 2-(2-methylbutyl)-2-propyl-1,3-propanediol or the at least one (Ia) alkoxylated derivative; and
1% to 99% by weight of 2-pentyl-2-propyl-1,3-propanediol or the at least one (IIa) alkoxylated derivative.

4. The polymer according to claim 2, wherein the mixture is obtained by
a) hydroformylating butene to pentanal and 2-methylbutanal,
b) subsequently aldol reacting the pentanal and 2-methylbutanal, with elimination of water, to 2-propylheptenal and 2-propyl-4-methylhexenal,
c) subsequently hydrogenating the 2-propylheptanal and 2-propyl-4-methylhexenal, to 2-propylheptanal and 2-propyl-4-methylhexanal, and
d) crossed Cannizzaro reacting the 2-propylheptanal and 2-propyl-4-methylhexanal and formaldehyde or, alternatively, aldol reacting the 2-propylheptenal and 2-propyl-4-methylhexenal of c) with formaldehyde and subsequently hydrogenating.

5. The polymer according to claim 1, comprising 0.5% to 70% by weight of 2-(2-methylbutyl)-2-propyl-1,3-propanediol, the at least one (Ia) alkoxylated derivative, or a mixture of 2-(2-methylbutyl)-2-propyl-1,3-propanediol or the at least one (Ia) alkoxylated derivative and 2-pentyl-2-propyl-1,3-propanediol of formula (II)

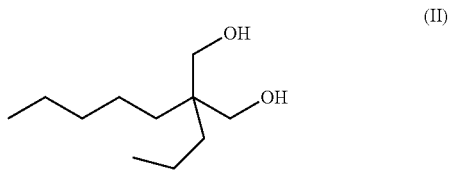

or (IIa) at least one alkoxylated derivative of 2-pentyl-2-propyl-1,3-propanediol.

6. A thermoplastic composition, comprising the polymer according to claim 1.

7. A molding, comprising the thermoplastic composition according to claim 6.

8. A coating composition, sealant, or adhesive, comprising the polymer according to claim 1.

9. The coating composition, sealant, or adhesive, according to claim 8, which is an aqueous composition.

10. A powder coating material, comprising the polymer according to claim 1.

11. A radiation-curable coating composition, comprising the polymer according to claim 1.

12. The polymer according to claim 3, wherein the mixture is obtained by
a) hydroformylating butene to pentanal and 2-methylbutanal,
b) subsequently aldol reacting the pentanal and 2-methylbutanal, with elimination of water, to 2-propylheptenal and 2-propyl-4-methylhexenal,
c) subsequently hydrogenating the 2-propylheptanal and 2-propyl-4-methylhexenal, to 2-propylheptanal and 2-propyl-4-methylhexanal, and
d) crossed Cannizzaro reacting the 2-propylheptanal and 2-propyl-4-methylhexanal and formaldehyde or, alternatively, aldol reacting the 2-propylheptenal and 2-propyl-4-methylhexenal of c) with formaldehyde, and subsequently hydrogenating.

13. The polymer according to claim 2, comprising 0.5% to 70% by weight of 2-(2-methylbutyl)-2-propyl-1,3-propanediol, the at least one (Ia) alkoxylated derivative, or the mixture.

14. The polymer according to claim 1, wherein the polyester contains carboxyl or carboxylate groups.

15. The polymer according to claim 1, wherein the polyester contains hydroxyl groups.

* * * * *